United States Patent [19]

Bull et al.

[11] 4,073,812

[45] Feb. 14, 1978

[54] BENZYL ETHERS

[75] Inventors: Michael J. Bull, Lower Halstow; Robert J. G. Searle, Sittingbourne, both of England

[73] Assignee: Shell Oil Company, Houston, Tex.

[21] Appl. No.: 773,355

[22] Filed: Mar. 1, 1977

[30] Foreign Application Priority Data

Mar. 5, 1976 United Kingdom ................. 8905/76

[51] Int. Cl.² ........................................... C07C 43/22
[52] U.S. Cl. .................................. 260/613 R; 424/341
[58] Field of Search ..................... 260/613 R; 424/341

[56] References Cited

U.S. PATENT DOCUMENTS 3,267,151  8/1966  Pillepich ........................... 260/613 R
3,600,437  8/1971  Marshall ...................... 260/613 R X

FOREIGN PATENT DOCUMENTS 2,516,515  10/1975  Germany ......................... 260/613 R Primary Examiner—Bernard Helfin

[57] ABSTRACT

Pesticidal benzyl ethers of the formula:

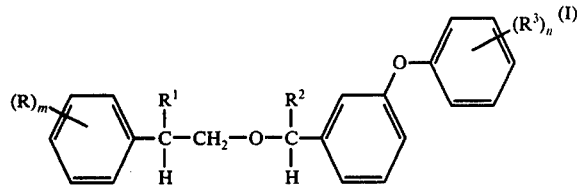

wherein each symbol has a meaning defined in the specification.

2 Claims, No Drawings

BENZYL ETHERS

DESCRIPTION OF THE INVENTION

It has been found that useful pesticidal activity is possessed by benzyl ethers of the formula

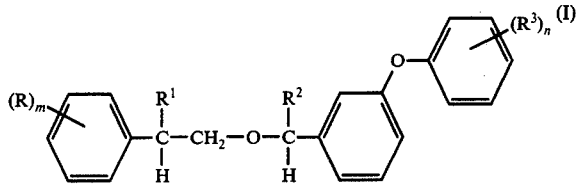

wherein $m$ is one or two, R is halogen, or is straight-chain or branched-chain alkyl or alkoxy of one to six carbon atoms, $R^1$ is branched-chain alkyl of three to six carbon atoms, $R^2$ is hydrogen or alkynyl of two to four carbon atoms, n is zero or 1, and $R^3$ is fluorine. The alkynyl moiety can be either straight-chain or branched-chain and the linking carbon atom can but need not be involved in the unsaturated linkage; ethynyl is a preferred alkynyl moiety.

Because the members thereof appear to have the highest insecticidal activity, the subgenus of the genus of Formula I wherein R is chlorine, methyl or methoxy, $R^1$ is isopropyl and $R^2$ is hydrogen is to be regarded as a preferred subgenus of these compounds.

These ethers possess one or more asymmetric carbon atoms and can thereby exist in different stereoisomeric forms. All such different stereoisomers, together with their racemic mixtures, fall within the scope of this invention.

Those ethers of Formula I in which $R^2$ is hydrogen may conveniently be prepared by reacting a compound of the formula:

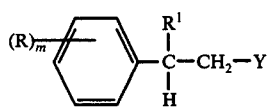

with a compound of the formula:

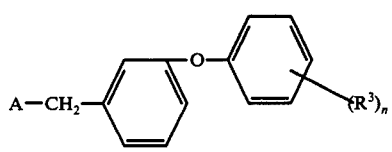

wherein one of Y and A represents a halogen, suitably chlorine, atom and the other represents the moiety O-met, in which met denotes an alkali metal atom, the other substituents having the meanings defined in Formula I. The reaction is suitably carried out in an organic solvent, such as toluene, and may be effected at any convenient temperature from room temperature up to the reflux temperature of the reaction mixture. The compound containing the O-met moiety may be prepared by appropriate adaption of conventional synthetic procedures, for example by reaction of the corresponding alcohol with an alkali metal hydride, suitably in an organic solution such as dimethylformamide and toluene.

The precursor (II) can be prepared by treating the corresponding acids (British Patent No. 1,021,014; Ag. Biol. Chem., 39, 267-272 (1975)) with lithium aluminum hydride in a solvent such as diethyl either at a moderately elevated temperature, for example at the reflux temperature, then treating the mixture with a base, such as sodium hydroxide solution. The product alcohol can be recovered by filtering the mixture, extracting with a solvent (diethyl ether is suitable), removing the solvent and using chromatographic techniques to purify the product (silica gel is a suitable adsorbant; methylene chloride and/or mixtures of methylene chloride and diethyl ether, are suitable eluents).

Those compounds of the invention wherein $R^2$ is alkynyl may be prepared by reacting the corresponding compound wherein $R^2$ is hydrogen with N-bromosuccinimide, suitably in a solvent such as carbon tetrachloride and in the presence of a free radical generator such as azo-bis-isobutyronitrile, and treating the resultant product with the appropriate alkynyl magnesium halide, such as ethynyl magnesium bromide.

The benzyl ethers of the invention are of interest as pesticides, particularly as tickicides, insecticides and acaricides for agricultural and domestic outlets. The invention therefore includes within its scope pesticidal compositions comprising a carrier and/or a surface-active agent together with, as active ingredient, a benzyl either of Formula I. Likewise the invention also includes a method combating tick, insect and/or acarid pests at a locus which comprises applying to the locus a pesticidally effective amount of a benzyl ether of Formula I or composition containing such a compound.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling. The carrier may be a solid or a fluid. Any of the materials usually applied in formulating pesticides may be used as the carrier.

Suitable solid carriers are natural and synthetic clays and silicates, for example natural silicas such as diatomaceous earths; magnesium silicates, for example, talcs; magnesium aluminum silicates, for example attapulgites and vermiculites; aluminum silicates, for example kaolinites, montmorillinites and micas; calcium carbonate; calcium sulphate; synthetic hydrated silicon oxides and synthetic calcium or aluminum silicates; elements such as for example, carbon and sulphur; natural and synthetic resins such as, for example coumarone resins, polyvinyl chloride and styrene polymers and copolymers; solid polychlorophenols; bitumen; waxes such as for example, beeswax, paraffin wax, and chlorinated mineral waxes; and solid fertilisers, for example superphosphates.

Examples of suitable fluid carriers are water, alcohols, such as for example, isopropanol; glycols; ketones such as for example, acetone, methyl ethyl ketone, methyl isobutyl ketone and cyclohexanone; ethers; aromatic hydrocarbons such as for example, benzene, toluene and xylene; petroleum fractions such as for example, kerosine; light mineral oils; chlorinated hydrocarbons, such as for example, carbon tetrachloride, perchloroethylene, trichloroethane, including liquefied normally vaporous gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides, fungicides, or insecticides may be used. Examples of suitable surface-active agents are the sodium or calcium salts of polyacrylic acids and lignin sulphonic acids; the condensation products of fatty acids of aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example, sodium lauryl sulphate, sodium secondary alkyl sulphates, sodium salts of sulphonated castor oil, and sodium alkylaryl sulphonates such as sodium dodecylbenzene sulphonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates and aerosols and will generally contain 0.5 to 95% w, preferably 0.5 to 75% w, of toxicant. Wettable powders are usually compounded to contain 25, 50 or 75% w of toxicant and usually contain, in addition to solid carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and are diluted in the field with further solid carrier to give a composition usually containing ½-10% w of toxicant. Granules are usually prepared to have a size between 10 and 100 BS mesh (1.676 - 0.152 mm), and may be manufactured by agglomeration or impregnation techniques. Generally, granules will contain ½-25% w toxicant and 0-10% w of additives such as stabilisers, slow release modifiers and binding agents. Emulsifiable concentrates usually contain, in addition to the solvent and, when necessary, co-solvent, 10-50% w/v toxicant, 2-20% w/v emulsifiers and 0-20% w/v of appropriate additives such as stabilisers, penetrants and corrosion inhibitors. Suspension concentrates are compounded so as to obtain a stable, non-sedimenting, flowable product and usually contain 10-75% w toxicant, 0.5 - 15% w of dispersing agents, 0.1 - 10% w of suspending agents such as protective colloids and thixotropic agents, 0 - 10% w of appropriate additives such as defoamers, corrosion inhibitors, stabilisers, penetrants and stickers, and as carrier, water or an organic liquid in which the toxicant is substantially insoluble; certain organic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick "mayonnaise"-like consistency.

The compositions of the invention may also contain other ingredients, for example, other compounds possessing pesticidal, for example insecticidal, acaricidal, herbicidal or fungicidal properties.

The invention is further illustrated in the following Examples which show preparation of individual species of the genus of Formula I. In all cases, the identities of the products and which show preparation of individual species of the genus of Formula I. In all cases, the identities of the product and of any intermediate involved, were confirmed by appropriate chemical and spectral anaylses.

EXAMPLE 1

3-phenoxybenzyl 2-(4-chlorophenyl)-2-isopropylethyl ether (1)

2.0 g of 2-(4-chlorophenyl)-3-methylbutanol in 10 ml of a 20% mixture of dimethylformamide and toluene was added over a 5 minute period to sodium hydride (0.8 g, 50% in oil) in 20 ml of toluene at 110°-120° C, and the mixture was stirred for 15 minutes. 3.0 g of 3-phenoxybenzyl bromide in 15 ml of toluene was then added over a 15 minute period and the mixture was gently refluxed for 2 hours, then was cooled and 10 ml of mineral spirits was added. The mixture was poured into ice/hydrochloric acid, extracted with ether, washed with sodium bicarbonate solution and dried ($MgSO_4$). The solvent was removed to give an orange oil, which was chromatographed on silica gel using 1:1 methylene dichloride:hexane as eluent to give 1.

EXAMPLE 2

Alpha-ethynyl-3-phenoxybenzyl 2-(4-chlorophenyl)-2-isopropylethyl ether (2)

3.8 g of 3-phenoxybenzyl 2-(4-chlorophenyl)-2-isopropylethyl ether, 1.8 g of N-bromosuccinimide and a few crystals of azo-bis-isobutyronitrile were stirred under reflux in 80 ml of carbon tetrachloride for 30 minutes. The mixture was cooled in an ice-bath, filtered and the solvent removed to give a pale orange oil. A solution of the oil in 10 ml of tetrahydrofuran was added over a 20 minute period to a solution of an acetylenic Grignard reagent (prepared by saturating a solution of 2.3 g of ethyl bromide and 0.5 g of magnesium in 35 ml of tetrahydrofuran with acetylene at 15° C) whilst bubbling a slow stream of acetylene through the mixture. The stirring was continued overnight at room temperature under a stream of nitrogen. The black reaction mixture was warmed to 70° C for 30 minutes, cooled and a saturated solution of 20 ml of ammonium chloride added, followed by ether and water. The mixture was filtered through a "Celite" bed to remove the black solid and the organic layer separated, washed successively with ammonium chloride, sodium bicarbonate, sodium hydroxide and dried ($MgSO_4$). Removal of the solvent gave a dark brown oil which was purified by chromatography on silica gel using 1:1 toluene: petroleum ether 60°-80° C as eluent, to give 2.

EXAMPLES 3-9

Following procedures similar to those described and demonstrated above, further compounds according to the invention were prepared, as listed in Table I, in which the compounds are identified by reference to Formula I, $R^1$ being isopropyl in all cases.

Table I

| Compound | m | R | $R^2$ | n | $R^3$ |
|---|---|---|---|---|---|
| 3 | 1 | 3-Cl | H | 0 | — |
| 4 | 1 | 3-$CH_3$— | H | 0 | — |
| 5 | 1 | 4-$CH_3O$— | H | 0 | — |
| 6 | 2 | 3,4-$(CH_3O)_2$ | H | 0 | — |

Table I-continued

| Compound | m | R | R² | n | R³ |
|---|---|---|---|---|---|
| 7 | 1 | 4-Cl | H | 1 | 4-F |
| *8 | 1 | 4-Cl | H | 0 | — |
| *9 | 1 | 4-Cl | H | 0 | — |

*Compound 8 is the S-(+) optical isomer of Compound 1, while Compound 9 is the R-(−) optical isomer. These compounds were prepared from the appropriate optical isomers of 2-(4-dichlorophenyl)-3-methylbutanol.

The insecticidal, acaricidal and tickicidal activity of the compounds according to the present invention was tested as follows:

I. A 1.0% by weight solution in acetone of the compound to be tested was prepared, and taken up in a micrometer syringe. Two to three-day old adult female house flies (*Musca domestica*) were anaesthetized with carbon dioxide, and 1 μl drop of the test solution was brushed off on the ventral abdomen of each 20 flies being treated. The treated flies were held for 24 hours in glass jars, each containing a little granulated sugar as food for the flies, and the percentage of dead and moribund individuals was then recorded.

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under-surface of the leaf with the above formulation. Spraying was effected with a spraying machine delivering 450 liters per hectare, the plants passing under the spray on a moving belt. Ten adult 1-2 week-old mustard beetles (*Phaedon cochleariae*) were placed on the spraying leaf of each turnip plant and ten apterous (6-day-old) vetch aphids (*Megoura viciae*) were placed on the sprayed leaf of each broad bean plant. The plants were then enclosed in glass cylinders fitted at one end with a muslin cap. Mortality counts were made after 24 hours.

III. In tests against glass house spider mites (*Tetranychus urticae*) leaf discs cut from French bean plants were sprayed in the manner described under II. One hour after spraying, the discs were inoculated with 10 adult mites. Mortality counts were made 24 hours after inoculation.

IV. The compounds were formulated as solutions or fine suspensions in water containing 20% by weight of acetone and 0.05% by weight of Triton D 100 as wetting agent. The formulations contained 0.6% by weight of the compound to be tested. Pairs of leaves are removed from board bean plants and placed on filter paper inside plastic petri dishes. Immediately prior to testing ten larvae of the Egyptian cotton leafworm (*Spodoptera littoralis*) are transferred onto the leaves and allowed to settle down. Larvae and leaves are sprayed together using a spraying machine delivering 340 liters/hectare, operated under the conveyor belt principle. After spraying the larvae are covered with a petri dish lid. After 24 hours, the percentage of dead and moribund larvae was recorded.

V. The compounds were formulated as solutions or fine suspensions in acetone containing 10% by weight of polyethylene glycol having an average molecular weight of 400. The formulations contained 0.1% by weight of the compound to be tested. One ml of the above-mentioned solution is applied evenly to a filter paper situated inside a petri dish. After the paper is sufficiently dry it is folded in half and partly crimped along the outer edge to form a packet. About 80–100 larval ticks (*Boophilus microplus*) are transferred into the packet which is then sealed completely. The packets are placed inside an incubator, maintained at 27° C and 80% relative humidity, before assessing mortality 24 hours later.

The results of these tests are shown in Table III in which the test species are identified by the initials noted above, and A denotes complete kill, B some kill and C no kill of the test species.

TABLE III

| Compound No. | Insecticidal Activity | | | | | |
|---|---|---|---|---|---|---|
| | M.d. | P.c. | S.l. | M.v. | T.u. | B.m. |
| 1 | A | A | A | A | C | A |
| 2 | C | C | C | A | C | A |
| 3 | B | B | C | A | C | A |
| 4 | C | A | C | A | C | A |
| 5 | A | B | C | A | C | A |
| 6 | C | A | C | A | B | A |
| 7 | B | C | B | A | C | A |

Activity of compounds of this invention with respect to corn earworms (*Heliothis zea*) was determined by a standarized procedure in which a solution of suspension of the test compound was sprayed on the foliage of broad bean plants, the foliage then was infested with larvae of the insects, mortality in the insects being noted later. All of Compounds 1 through 9 were found to be active with respect to the corn earworm larvae.

We claim:

1. A compound of the formula:

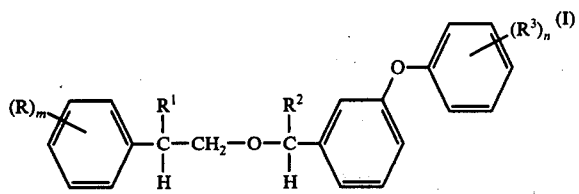

wherein $m$ is one or two, R is halogen, or is straight-chain or branched-chain alkyl or alkoxy of one to six carbon atoms, $R^1$ is branched-chain alkyl of three to six carbon atoms, $R^2$ is hydrogen or alkynyl of two to four carbon atoms, $n$ is zero or 1, and $R^3$ is fluorine.

2. A compound according to claim 1 wherein R is chlorine, methyl or methoxy, $R^1$ is isopropyl and $R^2$ is hydrogen.

* * * * *